US012582484B2

(12) United States Patent
Karanam et al.

(10) Patent No.: US 12,582,484 B2
(45) Date of Patent: Mar. 24, 2026

(54) AUTOMATIC PATIENT POSITIONING FOR MEDICAL EQUIPMENT

(71) Applicant: Shanghai United Imaging Intelligence Co., LTD., Shanghai (CN)

(72) Inventors: Srikrishna Karanam, Cambridge, MA (US); Meng Zheng, Cambridge, MA (US); Ziyan Wu, Cambridge, MA (US)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 768 days.

(21) Appl. No.: 17/957,382

(22) Filed: Sep. 30, 2022

(65) Prior Publication Data

US 2024/0108415 A1    Apr. 4, 2024

(51) Int. Cl.
| | |
|---|---|
| *A61B 34/20* | (2016.01) |
| *A61B 34/30* | (2016.01) |
| *A61G 13/02* | (2006.01) |
| *G06T 7/73* | (2017.01) |
| *G06T 17/20* | (2006.01) |
| *G16H 20/40* | (2018.01) |

(52) U.S. Cl.
CPC .............. *A61B 34/20* (2016.02); *A61B 34/30* (2016.02); *A61G 13/02* (2013.01); *G06T 7/73* (2017.01); *G06T 17/20* (2013.01); *G16H 20/40* (2018.01); *A61B 2034/2065* (2016.02); *A61G 2203/34* (2013.01); *G06T 2207/10024* (2013.01); *G06T 2207/10028* (2013.01); *G06T 2207/10048* (2013.01); *G06T 2207/20081* (2013.01); *G06T 2207/30196* (2013.01)

(58) Field of Classification Search
CPC . A61B 34/20; A61B 34/30; A61B 2034/2065; A61G 13/02; A61G 2203/34; G06T 2207/10024; G06T 2207/10028; G06T 2207/10048; G06T 2207/20081; G06T 2207/30196; G06T 7/73; G16H 20/40; G16T 17/20
See application file for complete search history.

(56) References Cited

U.S. PATENT DOCUMENTS

| | | | |
|---|---|---|---|
| 2010/0137882 A1* | 6/2010 | Quaid, III | .......... A61B 17/3403 606/130 |
| 2021/0118173 A1 | 4/2021 | Wu et al. | |

* cited by examiner

*Primary Examiner* — Camtu T Nguyen
(74) *Attorney, Agent, or Firm* — Zhong Law, LLC

(57) ABSTRACT

Disclosed is a method and a system for automatic positioning of a medical equipment with respect to a patient. The method includes obtaining sensor data related to the patient, from a plurality of sensors fixed relative to the medical equipment. The method further includes processing the sensor data to determine at least one pose characteristic of the patient and at least one shape characteristic of the patient. The method further includes determining at least one adjustment parameter for the medical equipment based on the at least one pose characteristic of the patient and the at least one shape characteristic of the patient. The method further includes adjusting the medical equipment based on the at least one adjustment parameter.

20 Claims, 5 Drawing Sheets

200

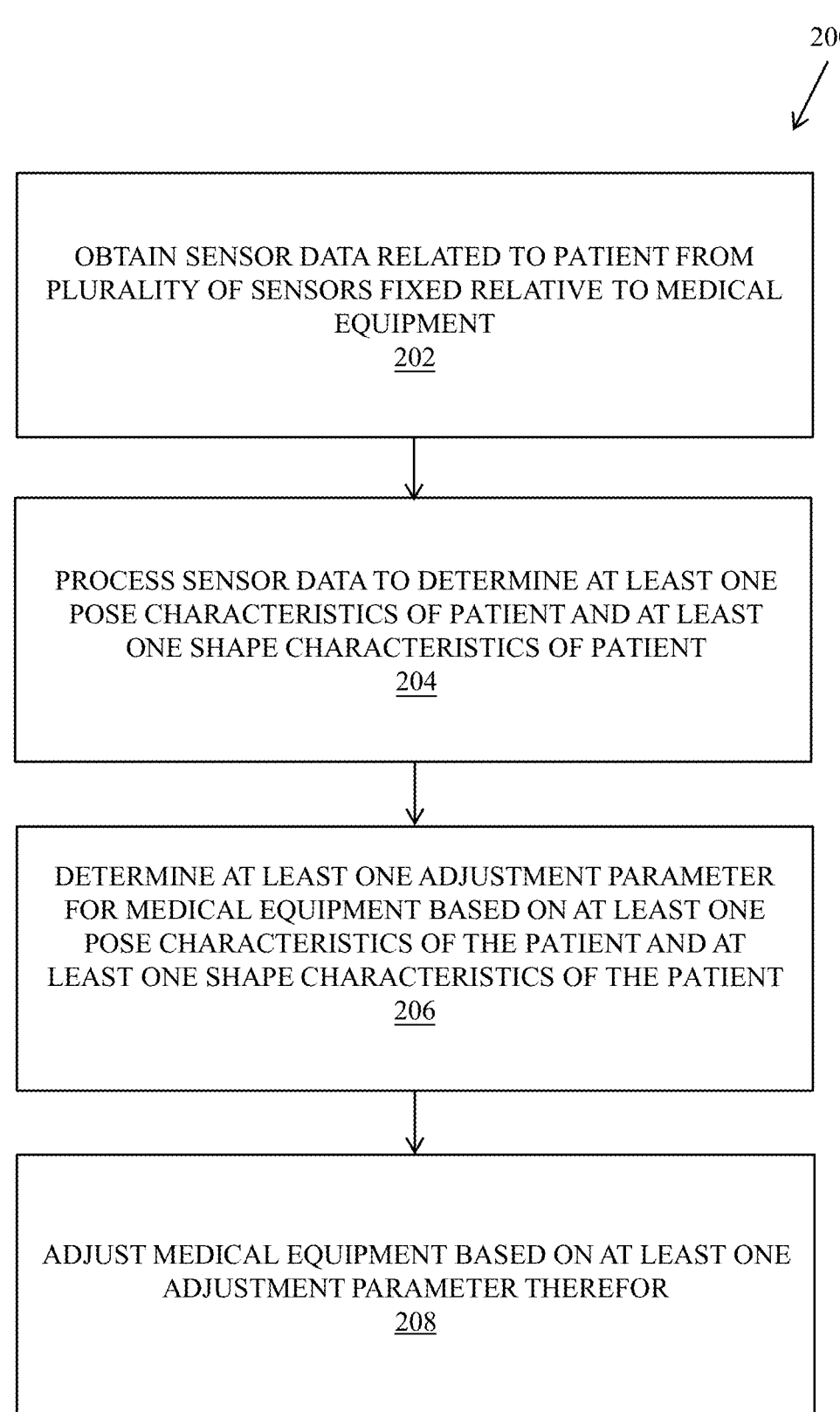

OBTAIN SENSOR DATA RELATED TO PATIENT FROM PLURALITY OF SENSORS FIXED RELATIVE TO MEDICAL EQUIPMENT
202

PROCESS SENSOR DATA TO DETERMINE AT LEAST ONE POSE CHARACTERISTICS OF PATIENT AND AT LEAST ONE SHAPE CHARACTERISTICS OF PATIENT
204

DETERMINE AT LEAST ONE ADJUSTMENT PARAMETER FOR MEDICAL EQUIPMENT BASED ON AT LEAST ONE POSE CHARACTERISTICS OF THE PATIENT AND AT LEAST ONE SHAPE CHARACTERISTICS OF THE PATIENT
206

ADJUST MEDICAL EQUIPMENT BASED ON AT LEAST ONE ADJUSTMENT PARAMETER THEREFOR
208

FIG. 2

AUTOMATIC PATIENT POSITIONING FOR MEDICAL EQUIPMENT

TECHNICAL FIELD

The aspects of the disclosed embodiments relate generally to medical, surgical, and/or robotic devices and systems; and in particular, to a system and a method for patient positioning, or more specifically for automatic positioning of a medical equipment with respect to a patient or person.

BACKGROUND

Minimally invasive medical techniques are intended to reduce the number of extraneous tissues which is damaged during diagnostic or surgical procedures, thereby reducing patient recovery time, discomfort, and deleterious side effects. However, only a portion of the current surgeries use these advantageous techniques due to limitations in minimally invasive surgical instruments and the additional surgical training involved in mastering them. Minimally invasive robotic surgical systems have been developed to increase a surgeon's dexterity and avoid some of the limitations on traditional minimally invasive techniques. In robotic surgery, the surgeon uses some form of remote control, e.g., a servomechanism or the like, to manipulate surgical instrument movements, rather than directly holding and moving the instruments by hand.

In robotic surgery, it is necessary to determine with high precision a coordinate location of the target region (and surrounding critical structures) in the body of a patient relative to the reference frame of the medical equipment. For example, in radio surgery, which refers to a procedure in which intense and precisely directed doses of radiation are delivered to a target region in a patient in order to destroy tumorous cells or otherwise treat the target region, it is necessary to control the position of the radiation source so that its beam can be precisely directed to the target tissue while minimizing irradiation of surrounding healthy tissue.

While new robotic surgery systems and devices have proven highly effective and advantageous, still further improvements would be desirable, especially for automatic positioning of a medical equipment with respect to the body of a patient. In light of the foregoing discussion, there exists a need for a system or a method for automatic positioning of a medical equipment with respect to the body or body part of a patient. Further limitations and disadvantages of conventional and traditional approaches will become apparent to one of skill in the art through comparison of such systems with some aspects of the present disclosure as set forth in the remainder of the present application with reference to the drawings.

SUMMARY

The aspects of the disclosed embodiments provide a system and a method for automatic positioning of medical equipment with respect to a patient, substantially as shown in and/or described in connection with at least one of the figures, as set forth more completely in the claims.

In an example, the aspects of the disclosed embodiments provide a method for automatic positioning of a medical equipment with respect to a patient. In one embodiment, the method includes obtaining sensor data related to the patient, from a plurality of sensors fixed relative to the medical equipment. The method further includes processing the sensor data to determine at least one pose characteristics of the patient and at least one shape characteristics of the patient. The method further includes determining at least one adjustment parameter for the medical equipment based on the at least one pose characteristics of the patient and the at least one shape characteristics of the patient. The method further includes adjusting the medical equipment based on the at least one adjustment parameter.

In a possible implementation form, processing the sensor data includes implementing a machine learning model to: estimate two-dimensional pixel coordinates of a predefined set of joints of the patient based on the sensor data; triangulate the two-dimensional pixel coordinates of the predefined set of joints of the patient to infer three-dimensional global coordinates of the predefined set of joints of the patient; generate a three-dimensional representation of the patient based on the three-dimensional global coordinates of the predefined set of joints of the patient; and process the three-dimensional representation of the patient to determine the at least one pose characteristics of the patient and the at least one shape characteristics of the patient.

In a possible implementation form, the three-dimensional representation includes one of: a parametric mesh model of the patient, a non-parametric mesh model of the patient.

In a possible implementation form, the method further includes training the machine learning model based on calibration information for each of the plurality of sensors for calculating reprojection error in corresponding sensor data. The method further includes implementing the trained machine learning model to compute a confidence score for each of the determined at least one pose characteristics of the patient and the determined at least one shape characteristics of the patient in consideration of the calculated reprojection errors in the sensor data.

In a possible implementation form, the method further includes updating the determined at least one pose characteristics of the patient and the determined at least one shape characteristics of the patient based on the respective confidence scores.

In a possible implementation form, the method further includes providing a user interface to allow a user to select one of: the determined at least one pose characteristics of the patient and the determined at least one shape characteristics of the patient, and the updated at least one pose characteristics of the patient and the updated at least one shape characteristics of the patient. The method further includes utilizing the selected one of: the determined at least one pose characteristics of the patient and the determined at least one shape characteristics of the patient, and the updated at least one pose characteristics of the patient and the updated at least one shape characteristics of the patient for determining the at least one adjustment parameter for the medical equipment.

In a possible implementation form, the medical equipment includes an articulated robotic arm. Herein, adjusting the medical equipment includes moving the articulated robotic arm to an initial coordinate position for performing a medical procedure based on the at least one adjustment parameter.

In a possible implementation form, the medical equipment includes a bed onto which the patient is placed. Herein, adjusting the medical equipment includes one or more of: tilting, translating, rotating the bed based on the at least one adjustment parameter.

In a possible implementation form, the plurality of sensors includes at least one of: one or more RGB sensors, one or more depth sensors, one or more infrared sensors.

In a possible implementation form, the plurality of sensors includes one or more pressure sensors embedded in the bed.

In another example, the aspects of the disclosed embodiments provide a system for automatic positioning of a medical equipment with respect to a patient. In one embodiment, the system includes a plurality of sensors fixed relative to the medical equipment, the plurality of sensors configured to generate sensor data related to the patient. The system further includes a processing arrangement configured to obtain the sensor data; process the sensor data to determine at least one pose characteristics of patient and at least one shape characteristics of the patient; determine at least one adjustment parameter for the medical equipment based on the at least one pose characteristics of the patient and the at least one shape characteristics of the patient; and adjust the medical equipment based on the at least one adjustment parameter.

In a possible implementation form, the processing arrangement is configured to implement a machine learning model to: estimate two-dimensional pixel coordinates of a predefined set of joints of the patient based on the sensor data; triangulate the two-dimensional pixel coordinates of the predefined set of joints of the patient to infer three-dimensional global coordinates of the predefined set of joints of the patient; generate a three-dimensional representation of the patient based on the three-dimensional global coordinates of the predefined set of joints of the patient; and process the three-dimensional representation of the patient to determine the at least one pose characteristics of the patient and the at least one shape characteristics of the patient.

In a possible implementation form, the three-dimensional representation includes one of: a parametric mesh model of the patient, a non-parametric mesh model of the patient.

In a possible implementation form, the processing arrangement is further configured to train the machine learning model based on calibration information for each of the plurality of sensors for calculating reprojection error in corresponding sensor data. The processing arrangement is further configured to implement the trained machine learning model to compute a confidence score for each of the determined at least one pose characteristics of the patient and the determined at least one shape characteristics of the patient in consideration of the calculated reprojection errors in the sensor data.

In a possible implementation form, the processing arrangement is further configured to update the determined at least one pose characteristics of the patient and the determined at least one shape characteristics of the patient based on the respective confidence scores.

In a possible implementation form, the system further includes a user interface to allow a user to select one of: the determined at least one pose characteristics of the patient and the determined at least one shape characteristics of the patient, and the updated at least one pose characteristics of the patient and the updated at least one shape characteristics of the patient. Herein, the processing arrangement is configured to utilize the selected one of: the determined at least one pose characteristics of the patient and the determined at least one shape characteristics of the patient, and the updated at least one pose characteristics of the patient and the updated at least one shape characteristics of the patient for determining the at least one adjustment parameter for the medical equipment.

In a possible implementation form, the medical equipment includes an articulated robotic arm. Herein, the processing arrangement is configured to adjust the medical equipment by moving the articulated robotic arm to an initial coordinate position for performing a medical procedure based on the at least one adjustment parameter.

In a possible implementation form, the medical equipment includes a bed onto which the patient is placed. Herein, the processing arrangement is configured to adjust the medical equipment by one or more of: tilting, translating, rotating the bed based on the at least one adjustment parameter.

In a possible implementation form, the plurality of sensors includes at least one of: one or more RGB sensors, one or more depth sensors, one or more infrared sensors.

In a possible implementation form, the plurality of sensors includes one or more pressure sensors embedded in the bed.

It is to be appreciated that all the aforementioned implementation forms can be combined. It has to be noted that all devices, elements, circuitry, units, and means described in the present application could be implemented in the software or hardware elements or any kind of combination thereof. All steps which are performed by the various entities described in the present application as well as the functionalities described to be performed by the various entities are intended to mean that the respective entity is adapted to or configured to perform the respective steps and functionalities. Even if, in the following description of specific embodiments, a specific functionality or step to be performed by external entities is not reflected in the description of a specific detailed element of that entity that performs that specific step or functionality, it should be clear for a skilled person that these methods and functionalities can be implemented in respective software or hardware elements, or any kind of combination thereof. It will be appreciated that features of the present disclosure are susceptible to being combined in various combinations without departing from the scope of the present disclosure as defined by the appended claims.

Additional aspects, advantages, features, and objects of the present disclosure would be made apparent from the drawings and the detailed description of the illustrative implementations construed in conjunction with the appended claims that follow.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams.

FIG. 2 is a flowchart of a method for automatic positioning of the medical equipment with respect to the patient, in accordance with an embodiment of the present disclosure;

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

Figure 1:
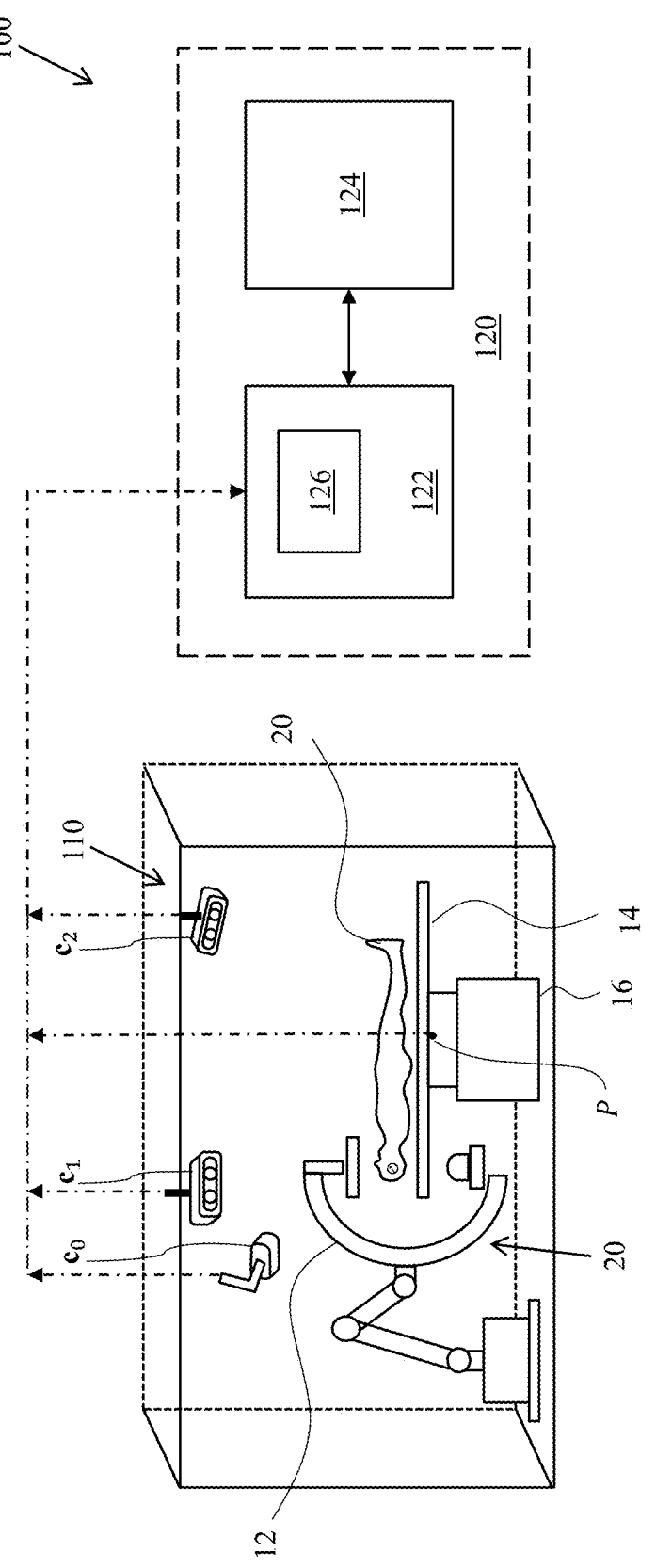
FIG. 1 is a block diagram of a system for automatic positioning of a medical equipment with respect to a patient, in accordance with an embodiment of the present disclosure.

Referring to FIG. 1, illustrated is a schematic diagram of a system (generally referred by the reference numeral 100) for automatic positioning of a medical equipment (as represented by reference numeral 10) with respect to the body of a patient (as represented by reference numeral 20). Generally, the body of a patient refers to the human body, or a part of the human body. In one embodiment, the automatic positioning of a medical equipment with respect to a patient includes obtaining sensor data related to the patient, from a plurality of sensors fixed relative to the medical equipment; processing the sensor data to determine at least one pose characteristics of the patient and at least one shape characteristics of the patient; determining at least one adjustment parameter for the medical equipment based on the at least one pose characteristics of the patient and the at least one shape characteristics of the patient; and adjusting the medical equipment based on the at least one adjustment parameter.

As used herein, the medical equipment 10 generally relates to medical robotic devices, including, but not limited to, surgical robots, radiosurgery robots, medical imaging robots, and the like.

In the exemplary illustration of FIG. 1, the medical equipment 10 is shown to include the robotic device in the form of an articulated robotic arm 12. Further, the medical equipment 10, as referred herein, includes a piece of furniture in the form of a bed 14 onto which a patient may lie down. In other examples, the medical equipment 10 may have other form of robotic device, such as an exosuit, and other form of furniture, such as a table, a chair or a couch, without departing from the spirit and the scope of the present disclosure. It may be appreciated that in medical procedures involving the medical equipment 10 being the medical robotic devices, it is necessary to have the patient, or at least region of the patient 20 of the patient on which the medical procedure is to be conducted, to be positioned at a precisely known location relative to the medical equipment 10 to initiate the medical procedure. For example, in radiosurgery, it is necessary to determine with precision the location of target region (and surrounding critical structures) of the patient 20 relative to the reference frame of the medical equipment 10, so as to control the position of the radiation source (as part of the medical equipment 10) such that its beam can be precisely directed to the target tissue while minimizing irradiation of surrounding healthy tissue.

The present system 100 is described for adjusting position of the patient 20 during, for example, therapeutic radiation treatment, using and as part of the medical equipment 10. In one implementation of the present disclosure, the medical equipment 10 may have the articulated robotic arm 12 configured to move its end-effector to a suitable initial position with respect to the patient 20 in consideration of a pose and a shape thereof, based on the medical procedure to be performed. In another implementation of the present disclosure, the medical equipment 10 may integrate a track mount assembly (generally shown with reference numeral 16) in the bed 14 to facilitate movement of the patient 20 in a three-dimensional (3D) space, as well raising and lowering the patient 20 to high and low positions without compromising the flexibility or positioning in translational and rotational movements. In an example, the track mount assembly 16 may be vertically mounted, for example, to a vertical side of a column in the bed 14 to facilitate the required movement of the patient 20.

As illustrated in FIG. 1, the system 100 includes a plurality of sensors (generally referred by reference numeral 110) configured to generate sensor data related to the patient 20. As used herein, the "sensor data related to the patient 20" refers to sensed data which may help determine one or more of size, shape, pose and position of the patient 20 with respect to the medical equipment 10. For this purpose, the plurality of sensors 110 are fixed relative to the medical equipment 10. This way, the one or more of size, shape, pose and position of the patient 20 as determined using the sensor data could provide a reference to be utilized for controlling positioning of the medical equipment 10. In an embodiment of the present system 100, the plurality of sensors 110 includes at least one of: one or more RGB sensors, one or more depth sensors, one or more infrared sensors. Herein, each of the plurality of sensors 110 may be an imaging device, such as a camera which may provide one, two or all of the said features of RGB sensing, depth sensing, infrared sensing. Further, in an embodiment of the present system, the plurality of sensors 110 may also include one or more pressure sensors 'P' (only one shown in the accompanied drawings) embedded in the bed 14 onto which the patient 20 is laid down. As may be contemplated by a person skilled in the art, the sensed pressure values, via the pressure sensor 'P', from the bed 14, may be used to determine one or more of shape, pose and position of the patient 20 with respect to the medical equipment 10 (as required, and discussed in more detail later in the disclosure).

In the illustrated example of FIG. 1, the system 100 is shown to include three imaging devices, a first imaging device 'C1', a second imaging device 'C2' and a third imaging device 'C3', as part of the plurality of sensors 110, which may be mounted at different locations in a room, such as an Operation Theatre (OT), say from one or more walls and ceiling of the OT, in which the medical equipment 10 is set-up for performing the medical procedure. Herein, the purpose of using multiple imaging devices 'C1', 'C2' and 'C3' is to counteract effect of any occlusion in the set-up because of presence of any object, so that a combined image from the used multiple imaging devices 'C1', 'C2' and 'C3' may provide an unobstructed view of the patient 20 with respect to the medical equipment 10 so as to determine its relative position and/or pose therewith. It may be understood that although three image sensors 'C1', 'C2' and 'C3' have been shown in the exemplary set-up; in other examples, the number of used imaging devices may vary depending on the set-up of the medical equipment 10.

As illustrated in FIG. 1, the system 100 includes a computing device (represented by reference numeral 120) for enabling automatic positioning of the medical equipment 10 with respect to the patient 20. The term 'computing device' as used herein refers to a structure and/or module that includes programmable and/or non-programmable components configured to store, process and/or share information and/or signals for automatic positioning of the medical equipment 10 with respect to the patient 20. The computing device 120 may be a controller having elements, such as a display, control buttons or joysticks, processors, memory and the like. In the present examples, the computing device 120 may include components such as memory, a processor, a network adapter and the like, to store, process and/or share information with other computing components, such as, a remote server, a remote gateway, a network, or a database. Optionally, the computing device 120 may be supplemented with additional computation system, such as neural networks, and hierarchical clusters of pseudo-analog variable state machines implementing artificial intelligence algorithms. Optionally, the computing device 120 may be implemented as a computer program that provides various services (such as, database service) to other devices, modules or apparatuses. Examples of the computing device 120 include, but are not limited to, a workstation, a desktop computer, a mobile computer, a laptop computer, a netbook computer, a tablet computer, a smart phone, a personal digital assistant (PDA), and the like.

The computing device 120, as part of the system 100, includes a processing arrangement 122. The processing arrangement 122 is disposed in signal communication with each of the plurality of sensors 110 to obtain the generated sensor data therefrom. In embodiments of the present disclosure, the processing arrangement 122 is configured to process the sensor data to determine at least one pose characteristics of patient 20 and at least one shape characteristics of the patient 20; determine at least one adjustment parameter for the medical equipment 10 based on the at least one pose characteristics of the patient 20 and the at least one shape characteristics of the patient 20; and adjust the medical equipment 10 based on the at least one adjustment parameter, which is the objective of the present disclosure. This way the medical equipment 10 can be adjusted, for example by moving the articulated robotic arm 12 to an initial coordinate position and/or by one or more of: tilting, translating, rotating the bed 14, so as to be able to perform the medical procedure on the patient 20.

It may be understood that the term "processing arrangement" as used herein refers to a structure and/or module that includes programmable and/or non-programmable components configured to store, process and/or share information and/or signals for automatic positioning of the medical equipment 10 with respect to the patient 20. Optionally, the processing arrangement 122 includes any arrangement of physical or virtual computational entities capable of enhancing information to perform various computational tasks. Optionally, the processing arrangement 122 is supplemented with additional computation systems, such as neural networks, and hierarchical clusters of pseudo-analog variable state machines implementing artificial intelligence algorithms. In the present examples, the processing arrangement 122 may include components such as memory, a controller, a network adapter and the like, to store, process and/or share information with other components, such as a current sensor, a voltage sensor, a remote server unit, a database. Optionally, the processing arrangement 122 is implemented as a computer program that provides various services (such as database service) to other devices, modules or apparatus. Moreover, the processing arrangement 122 refers to a computational element that is operable to respond to and processes instructions for management of the electric grid. Optionally, the processing arrangement 122 includes, but is not limited to, a microcontroller, a micro-controller, a complex instruction set computing (CISC) microcontroller, a reduced instruction set (RISC) microcontroller, a very long instruction word (VLIW) microcontroller, Field Programmable Gate Array (FPGA) or any other type of processing circuit, for example as aforementioned.

The computing device 120, as part of the system 100, further includes a display device 124 to provide a user interface (hereinafter, referred by the same reference numeral 124 as the display device) to allow a user to control/manipulate the automatic positioning of the medical equipment 10 with respect to the patient 20. As used herein, the term "user" refers to a person (i.e., a human being) who may control the medical equipment 10 for performing the medical procedure. Such control by the user over the automatic positioning of the medical equipment 10 is required to correct/override by user-in-the-loop refinement procedure to refine the shape predictions by the present system 100 (as discussed later). Herein, the refined set, as may be provided by the user, is used to generate the control signals needed for final adjustment of the medical equipment 10 for automatic positioning of the medical equipment 10 with respect to the patient 20. In the present embodiments, the user input may be in the form of commands from an input device, such as a touch screen, keyboard, mouse, joystick, etc. (not shown) associated with the computing device 120, without any limitations.

Referring to FIG. 2, illustrated is a flowchart listing steps involved in a method 200 for automatic positioning of the medical equipment 10 with respect to the patient 10, in accordance with an embodiment of the present disclosure. The method 200 is implemented by the computing device 120, and specifically by use of the processing arrangement 122 and the display device 124 therein. As shown, the method 200 comprises the steps 202, 204, 206 and 208. The steps 202 to 208 are only illustrative and other alternatives can also be provided where one or more steps are added, one or more steps are removed, or one or more steps are provided in a different sequence without departing from the scope of the claims herein. Further, in some examples, the steps 202, 204, 206 and 208 may not necessarily be performed in sequential order.

At step 202, the method 200 includes obtaining the sensor data related to the patient 20, from the plurality of sensors 110 fixed relative to the medical equipment 10. Herein, the processing arrangement 122 is configured to obtain the sensor data related to the patient 20. As discussed, the processing arrangement 122 is disposed in signal communication with each of the plurality of sensors 110 to obtain the generated sensor data therefrom.

At step 204, the method 200 includes processing the sensor data to determine at least one pose characteristics of the patient 20 and at least one shape characteristics of the patient 20. Herein, the processing arrangement 122 is configured to process the sensor data to determine at least one pose characteristics of the patient 20 and at least one shape characteristics of the patient 20. In the present embodiments, the processing arrangement 122 is configured to implement a machine learning model (as represented by reference numeral 126) for this purpose. In the present embodiments, the machine learning model 126 is a convolutional neural network, or CNN (with two terms being interchangeably used hereinafter), which is a deep learning neural network designed for processing structured arrays of data. The construction of the CNN 126 is a multi-layered feed-forward neural network, made by assembling many unseen layers on top of each other in a particular order. Usually, the CNN 126 contains many convolutional layers assembled on top of each other, each one competent of recognizing more sophisticated shapes. The CNN 126 is very satisfactory at picking up on design in the input image, such as lines, gradients, circles, or even eyes and faces. This characteristic makes the CNN 126 so robust for computer vision.

In the present disclosure, the machine learning model 126 is configured to: estimate two-dimensional pixel coordinates of a predefined set of joints of the patient 20 based on the sensor data; triangulate the two-dimensional pixel coordinates of the predefined set of joints of the patient 20 to infer three-dimensional global coordinates of the predefined set of joints of the patient 20; generate a three-dimensional representation of the patient 20 based on the three-dimensional global coordinates of the predefined set of joints of the patient 20; and process the three-dimensional representation of the patient 20 to determine the at least one pose characteristics of the patient 20 and the at least one shape characteristics of the patient 20. Herein, the processing arrangement 122 is further configured to train the machine learning model 126 based on calibration information for each of the plurality of sensors 110 for calculating reprojection error in corresponding sensor data. The processing arrangement 122 is further configured to implement the trained machine learning model 126 to compute a confidence score for each of the determined at least one pose characteristics of the patient 20 and the determined at least one shape characteristics of the patient 20 in consideration of the calculated reprojection errors in the sensor data. The processing arrangement 122 is further configured to update the determined at least one pose characteristics of the patient 20 and the determined at least one shape characteristics of the patient 20 based on the respective confidence scores. This workflow has been described in reference to descriptions of FIG. 3 in the proceeding paragraphs.

Figure 3:
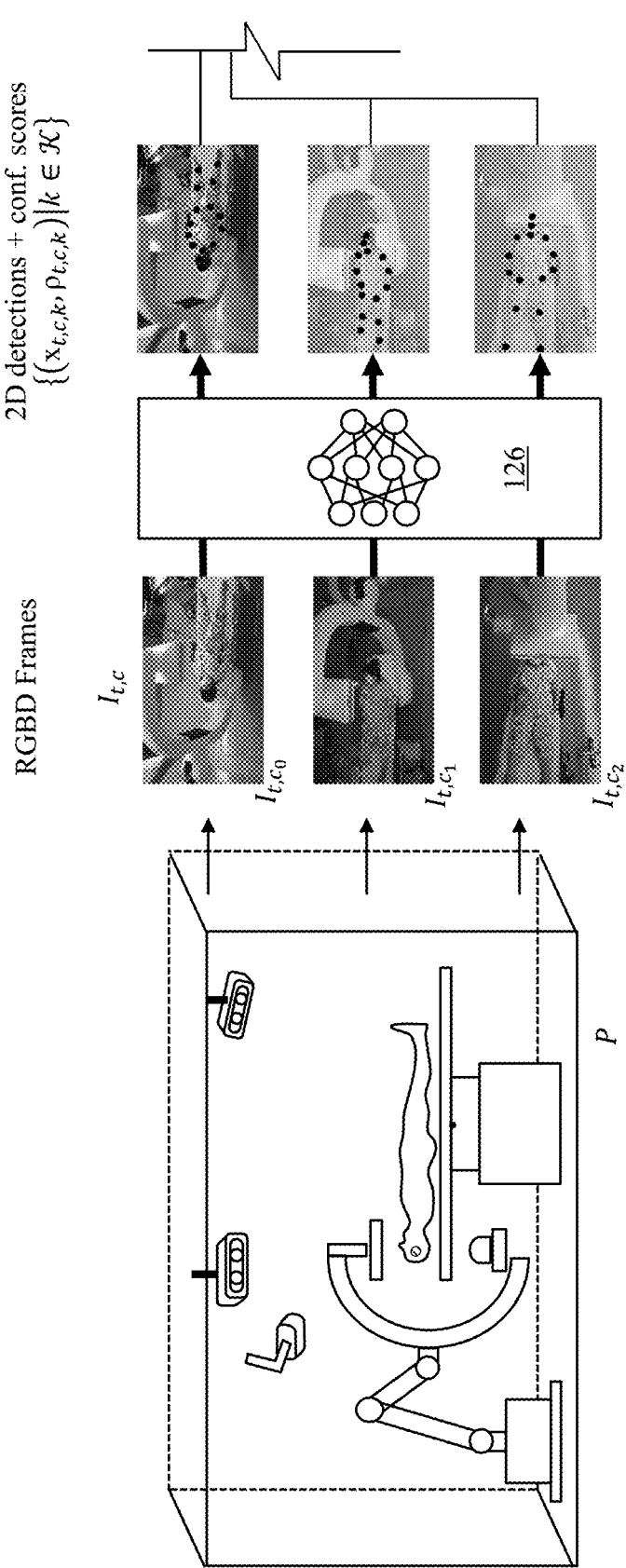
FIG. 3 is a schematic diagram of an overall workflow for automatic positioning of the medical equipment with respect to the patient, in accordance with an embodiment of the present disclosure.
Figure 3:
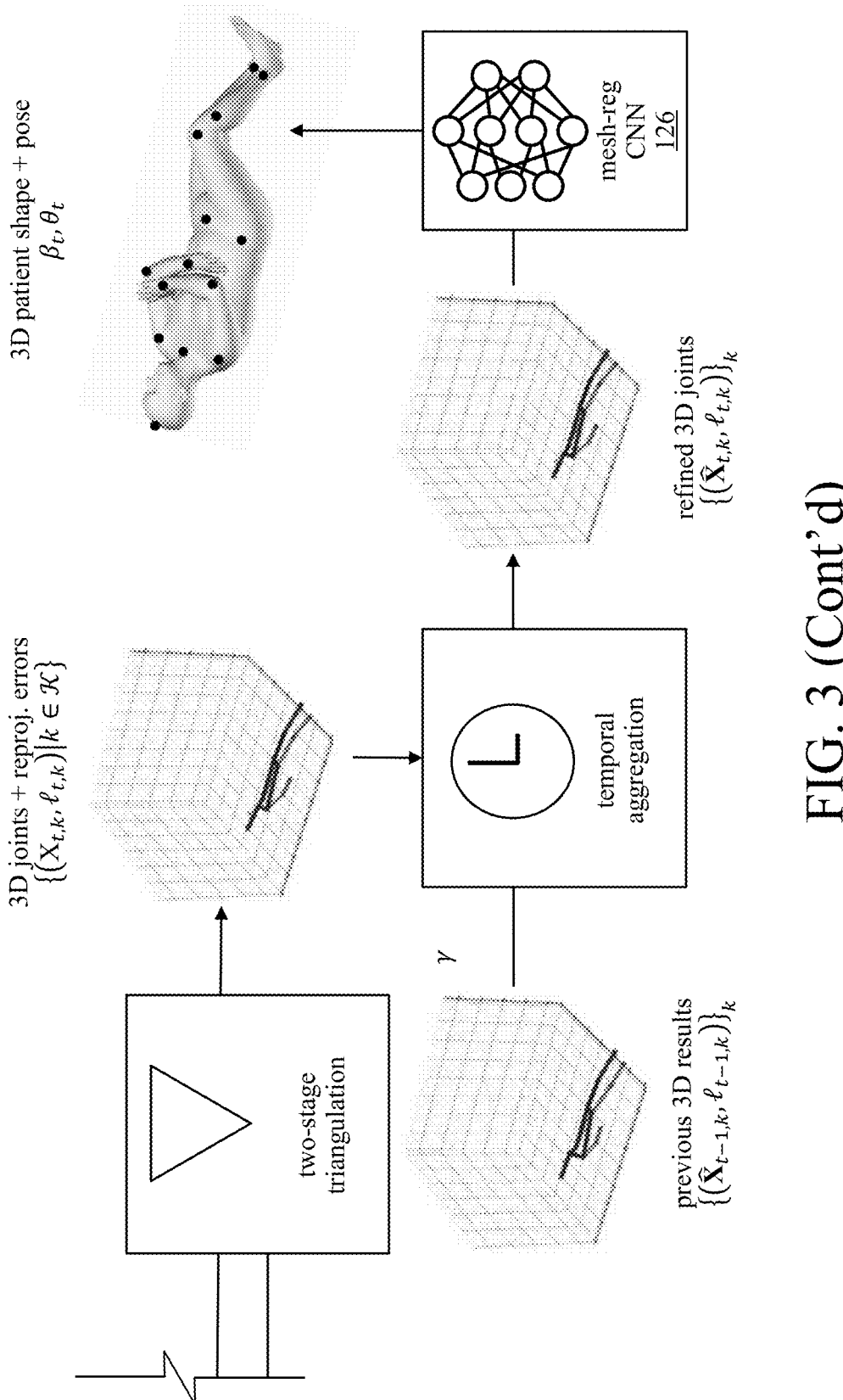

Referring to FIG. 3, as shown, the plurality of sensors 'C1', 'C2', 'C3' and 'P' provides sensor data in the form of RGBD frames of captured views of the patient 20 from different angles. These RGBD frames are fed to the machine learning model 126. That is, the machine learning model 126 takes RGB or RGB plus depth/infrared sensor data (images) from the sensors 'C1', 'C2', 'C3' and 'P' installed in the medical environment. The machine learning model 126 infers 2D patient body joint locations (a predefined set of patient joints, e.g., head top, shoulders, hips, etc.) in each of the RGBD image based on its training (which may be contemplated and thus not discussed herein). The machine learning model 126 further computes a corresponding confidence score of each joint location prediction. Herein, the processing of the sensor data to compute the confidence score is implemented by a specially trained module of the machine learning model 126 for this purpose. The computed confidence score may involve training the machine learning model 126 with data from multiple RGB sensors. Specifically, the training process may involve the use of calibration information for each of the plurality of sensors 110 to compute the reprojection errors for each predicted 2D joints. Given the predicted 2D joints and reprojected 2D joints, the training process may involve a loss function that measures the weighted deviations between the prediction and reprojection values. In an embodiment, one instantiation of the loss function may look like:

$$L = \Sigma w_i (x_i - y_i)^2$$

where $w_i$ is the confidence score predicted by the machine learning model for the corresponding predicted 2D keypoints $x_i$ and $y_i$ is the reprojected value of $x_i$ (i.e., use the $x_i$ from multiple views to compute the corresponding value of $x_i$ in 3D, and then use that 3D location to reproject to each of the RGBD views).

In the present examples, the computed confidence score may be a scalar value representing the overall prediction confidence of the trained machine learning model 126 across all the computed patient characteristics. In particular, the computed confidence score may be one scalar value for every computed patient characteristic. More specifically, the computed confidence score may be one scalar value for every detected 2D key point on each of the RGBD images.

In an example, the data from plurality of sensors 110 may be processed by one module of the machine learning model 126 to generate intermediate data representations. The intermediate data representations may then be processed by another module of the machine learning model 126 to compute the three-dimensional shape representation of the patient 20. Herein, the intermediate data representation may be a surface normal. In particular, the sensor data from each of the plurality of sensors 110 may be processed by the machine learning model 126 to give a corresponding surface normal representation. The surface normal representations from the sensor data of the plurality of sensors 110 may then be fused to give one fused surface normal. Herein, the fusion process may be achieved by the trained machine learning model 126 itself.

Figure 4:
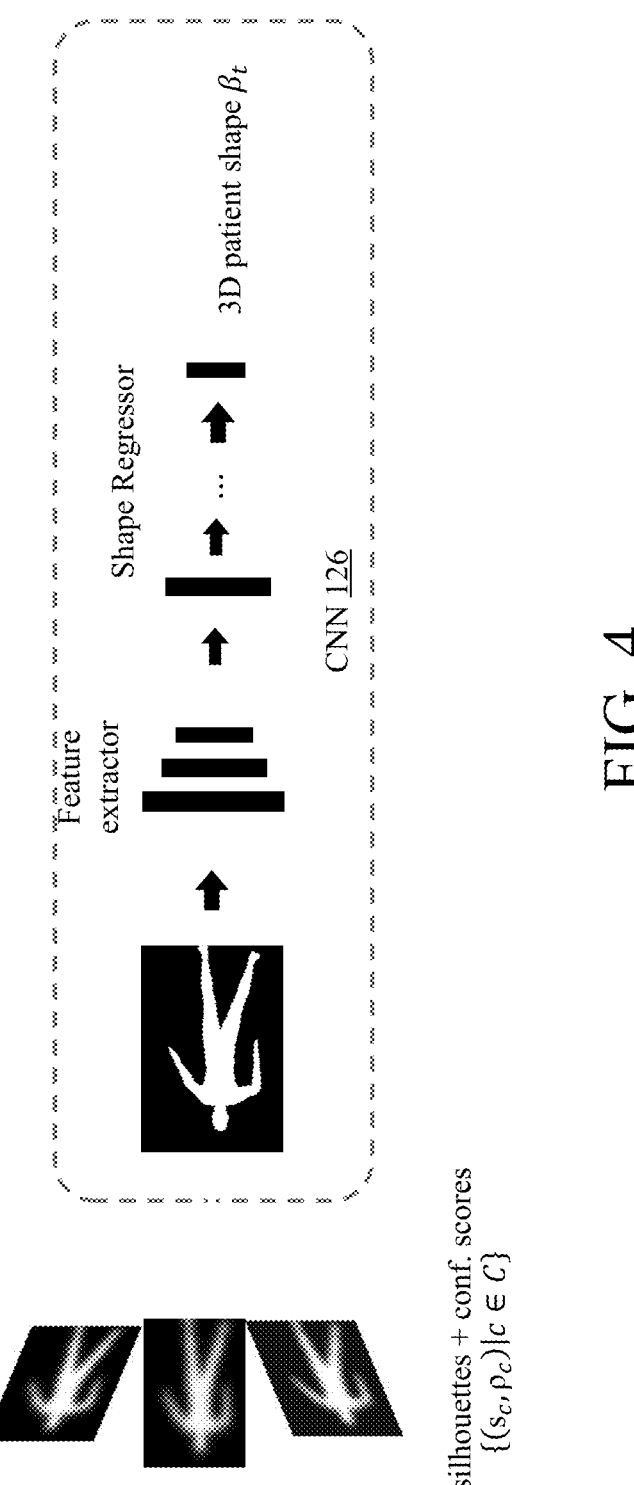
FIG. 4 is a schematic diagram of a process for generating a three-dimensional representation of the patient, in accordance with various embodiments of the present disclosure.

Given the 2D body joint location (in pixel) prediction in each RGBD image, a two-stage triangulation (a mathematical computation) is performed to infer 3D patient body joint location in a global coordinate system, based on given sensor calibration parameters. In the present examples, as discussed, a loss function is used for mathematical computation in the triangulation step, for inferring 3D body joint location in the global coordinate system from the 2D body joint location from different sensors. The triangulated 3D body joint locations are then further processed by the trained machine learning model 126 for pose or pose and shape characteristic estimation of the patient mesh model. In particular, the machine learning model 126 processing the intermediate representation (e.g., surface normal), uses the previous 3D results and by temporal aggregation, may output at least one characteristic of the patient which may be a patient body model. Herein, for more accurate shape characteristic estimation, the machine learning model 126 may be specifically trained, which takes in body geometry, e.g. contour or silhouettes, and corresponding confidence scores to predict the final shape characteristic of the patient 20. As illustrated in FIG. 4, the machine learning model 126 processes the determined shape characteristic of the patient 120, by implementation of feature extractor and shape regressor, to generate a three-dimensional representation of the of the patient 20. Such implementation may be contemplated by a person skilled in the art of machine learning and image processing, and thus not explained herein for brevity of the present disclosure. In the present embodiments, the three-dimensional representation may be one of a parametric mesh model of the patient 20 and a non-parametric mesh model of the patient 20.

At step 206, the method 200 includes determining at least one adjustment parameter for the medical equipment 10 based on the at least one pose characteristics of the patient 20 and the at least one shape characteristics of the patient 20. That is, the processing arrangement 122 is further configured to determine at least one adjustment parameter for the medical equipment 10 based on the at least one pose characteristics of the patient 20 and the at least one shape characteristics of the patient 20. Further, at step 208, the method 200 includes adjusting the medical equipment 10 based on the at least one adjustment parameter. That is, the processing arrangement 122 is further configured to adjust the medical equipment based on the at least one adjustment parameter. Herein, based on the determined pose and shape characteristics of the patient 20, the medical equipment 10 is adjusted, for instance by moving the articulated robotic arm 12 to an initial coordinate position and/or by adjusting the bed 14, so as to be able to perform the medical procedure on the patient 20. In an example, the processing arrangement 122 is configured to adjust the medical equipment 10 by moving the articulated robotic arm 12 to an initial coordinate position for performing a medical procedure based on the at least one adjustment parameter. In another example, the processing arrangement 122 is configured to adjust the medical equipment 10 by one or more of: tilting, translating, rotating the bed 14 based on the at least one adjustment parameter.

In the present embodiments, the processing arrangement 122 is further configured to update the determined at least one pose characteristics of the patient 20 and the determined at least one shape characteristics of the patient 20 based on the respective confidence score. In an embodiment, the system 100 provides the user interface 124 to allow the user to select one of: the determined at least one pose characteristics of the patient 20 and the determined at least one shape characteristics of the patient 20, and the updated at least one pose characteristics of the patient 20 and the updated at least one shape characteristics of the patient 20. Further, herein, the processing arrangement 122 is configured to utilize the selected one of: the determined at least one pose characteristics of the patient 20 and the determined at least one shape characteristics of the patient 20, and the updated at least one pose characteristics of the patient 20 and the updated at least one shape characteristics of the patient 20 for determining the at least one adjustment parameter for the medical equipment 10. For example, in certain circumstances, the user may feel one specific sensor may not be reliable; the user can then input or select the specified sensor through the user interface 124, the processing arrangement 122 will process the user input, and perform triangulation or shape characteristic estimation (as mentioned above) without considering the selected sensor data (i.e., confidence score for that sensor data is set to 0).

The present disclosure consider the problem of automatic positioning of the body of a human being (or patient) with respect to a medical equipment using data from multiple sensors. Given data from the multiple sensors, the present disclosure predicts confidence values for each associated patient characteristic (e.g., 2D key points, theta/beta mesh parameters, etc.) and then refines the initial patient characteristics to obtain a refined/finetuned set of characteristics. The present disclosure further predicts certain characteristics associated with patient shape (e.g., beta mesh parameters, shape binary silhouette, etc.) and then refines the initial patient characteristics by means of input from a user of the medical equipment to obtain a refined/finetuned set of characteristics. The refined set is then used to generate the control signals needed to automatically adjust the medical equipment to position the patient for performing the medical procedure.

Existing automatic positioning systems directly use the predictions of machine learning models without taking into consideration the underlying confidence of the machine learning model in making those predictions. Further, existing automatic positioning systems use shape predictions from single-view algorithms. Since one may have a multi-view setup in many applications, the known systems are not able to utilize this additional information to refine the shape predictions. The present disclosure use multi-view information to produce intermediate representations that are more complete (e.g., reduced occlusions impact) when compared to single-view intermediate representations, and propose the use of a machine learning model to predict patient shape parameters from these intermediate representations and to fuse multi-view intermediate representations into a single set of intermediate representations. The present disclosure provides the predicted confidence values to refine the initial predictions of the patient characteristics, and can also involve a human user-in-the-loop to investigate the predicted confidence values and use only those patient characteristics that the user is most interested in for the particular application.

The aspects of the disclosed embodiments are also directed to a computer program product with a non-transitory computer-readable storage medium comprising instructions which, when executed by a processor or computer, cause the processor or computer to carry out the steps of the implementations forms described herein, or method 200, for automatic positioning of a medical equipment with respect to a patient. Examples of implementation of the non-transitory computer-readable storage medium include, but is not limited to, Electrically Erasable Programmable Read-Only Memory (EEPROM), Random Access Memory (RAM), Read Only Memory (ROM), Hard Disk Drive (HDD), Flash memory, a Secure Digital (SD) card, Solid-State Drive (SSD), a computer readable storage medium, and/or CPU cache memory. A computer readable storage medium for providing a non-transient memory may include, but is not limited to, an electronic storage device, a magnetic storage device, an optical storage device, an electromagnetic storage device, a semiconductor storage device, or any suitable combination of the foregoing.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural. The word "exemplary" is used herein to mean "serving as an example, instance or illustration". Any embodiment described as "exemplary" is not necessarily to be construed as preferred or advantageous over other embodiments and/or to exclude the incorporation of features from other embodiments. The word "optionally" is used herein to mean "is provided in some embodiments and not provided in other embodiments". It is appreciated that certain features of the present disclosure, which are, for clarity, described in the context of separate embodiments, may also be provided in combination in a single embodiment. Conversely, various features of the present disclosure, which are, for brevity, described in the context of a single embodiment, may also be provided separately or in any suitable combination or as suitable in any other described embodiment of the disclosure.

The invention claimed is:

1. A method for automatic positioning of a medical equipment with respect to a patient, the method comprising:
obtaining sensor data related to the patient from a plurality of sensors fixed relative to the medical equipment;
estimating two-dimensional pixel coordinates of a predefined set of joints of the patient based on the sensor data;
triangulating the two-dimensional pixel coordinates of the predefined set of joints of the patient to infer three-dimensional global coordinates of the predefined set of joints of the patient; and
determining at least one pose characteristic of the patient and at least one shape characteristic of the patient based on the three-dimensional global coordinates of the predefined set of joints of the patient.

2. The method according to claim 1, further comprising generating a three-dimensional representation of the patient.

3. The method according to claim 2, wherein the three-dimensional representation comprises one of: a parametric mesh model of the patient or a non-parametric mesh model of the patient.

4. The method according to claim 2 further comprising:
training a machine learning model based on calibration information for each of the plurality of sensors for calculating reprojection error in corresponding sensor data; and
implementing the trained machine learning model to compute a confidence score for each of the determined at least one pose characteristic of the patient and the determined at least one shape characteristic of the patient in consideration of the calculated reprojection errors in the corresponding sensor data.

5. The method according to claim 4 further comprising updating the determined at least one pose characteristic of the patient and the determined at least one shape characteristic of the patient based on the respective confidence scores.

6. The method according to claim 5 further comprising:
providing a user interface to allow a user to select one of:
the determined at least one pose characteristic of the patient and the determined at least one shape characteristic of the patient, and the updated at least one pose characteristic of the patient and the updated at least one shape characteristic of the patient; and
utilizing the selected one of: the determined at least one pose characteristic of the patient and the determined at least one shape characteristic of the patient, and the updated at least one pose characteristic of the patient and the updated at least one shape characteristic of the patient for determining the at least one adjustment parameter for the medical equipment.

7. The method according to claim 1, wherein the medical equipment comprises an articulated robotic arm, and wherein adjusting the medical equipment comprises moving the articulated robotic arm to an initial coordinate position for performing a medical procedure based on the at least one adjustment parameter.

8. The method according to claim 1, wherein the medical equipment comprises a bed, and wherein adjusting the medical equipment comprises one or more of: tilting, translating, or rotating the bed based on the at least one adjustment parameter.

9. The method according to claim 1, wherein the plurality of sensors comprises at least one of: an RGB sensor, a depth sensor, or an infrared sensor.

10. The method according to claim 8, wherein the plurality of sensors comprises one or more pressure sensors embedded in the bed.

11. A system for automatic positioning of a medical equipment with respect to a patient, the system comprising:
a plurality of sensors fixed relative to the medical equipment, the plurality of sensors configured to generate sensor data related to the patient;
a processing arrangement configured to:
obtain the sensor data;
estimate two-dimensional pixel coordinates of a predefined set of joints of the patient based on the sensor data;
triangulate the two-dimensional pixel coordinates of the predefined set of joints of the patient to infer three-dimensional global coordinates of the predefined set of joints of the patient; and
determine at least one pose characteristic of the patient and at least one shape characteristic of the patient based on the three-dimensional global coordinates of the predefined set of joints of the patient.

12. The system according to claim 11, wherein the processing arrangement is further configured to
generate a three-dimensional representation of the patient.

13. The system according to claim 12, wherein the three-dimensional representation comprises one of: a parametric mesh model of the patient or a non-parametric mesh model of the patient.

14. The system according to claim 12, wherein the processing arrangement is further configured to:
train a machine learning model based on calibration information for each of the plurality of sensors for calculating reprojection error in corresponding sensor data; and
implement the trained machine learning model to compute a confidence score for each of the determined at least one pose characteristics of the patient and the determined at least one shape characteristics of the patient in consideration of the calculated reprojection errors in the corresponding sensor data.

15. The system according to claim 14, wherein the processing arrangement is further configured to update the determined at least one pose characteristics of the patient and the determined at least one shape characteristic of the patient based on the respective confidence scores.

16. The system according to claim 15 further comprising:
a user interface to allow a user to select one of: the determined at least one pose characteristic of the patient and the determined at least one shape characteristic of the patient, and the updated at least one pose characteristic of the patient and the updated at least one shape characteristic of the patient,
wherein the processing arrangement is configured to utilize the selected one of: the determined at least one pose characteristic of the patient and the determined at least one shape characteristic of the patient, and the updated at least one pose characteristic of the patient and the updated at least one shape characteristic of the patient for determining the at least one adjustment parameter for the medical equipment.

17. The system according to claim 11, wherein the medical equipment comprises an articulated robotic arm, and wherein the processing arrangement is configured to adjust the medical equipment by moving the articulated robotic arm to an initial coordinate position for performing a medical procedure based on the at least one adjustment parameter.

18. The system according to claim 11, wherein the medical equipment comprises a bed configured to have the patient placed thereon, and wherein the processing arrangement is configured to adjust the medical equipment by one or more of: tilting, translating, or rotating the bed based on the at least one adjustment parameter.

19. The system according to claim 11, wherein the plurality of sensors comprises at least one of: an RGB sensor, a depth sensor, or an infrared sensor.

20. The system according to claim 18, wherein the plurality of sensors comprises one or more pressure sensors embedded in the bed.

* * * * *